(12) United States Patent
Hirokane et al.

(10) Patent No.: US 8,398,600 B2
(45) Date of Patent: Mar. 19, 2013

(54) PREFILLED SYRINGE

(75) Inventors: Takeshi Hirokane, Hiratsuka (JP); Yoshio Aoki, Hiratsuka (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 20 days.

(21) Appl. No.: 12/519,193

(22) PCT Filed: Dec. 17, 2007

(86) PCT No.: PCT/JP2007/074215
§ 371 (c)(1), (2), (4) Date: Jun. 15, 2009

(87) PCT Pub. No.: WO2008/075639
PCT Pub. Date: Jun. 26, 2008

(65) Prior Publication Data
US 2010/0106096 A1    Apr. 29, 2010

(30) Foreign Application Priority Data
Dec. 20, 2006 (JP) .................. 2006-342764

(51) Int. Cl.
*A61M 5/00* (2006.01)
*C08G 63/02* (2006.01)
(52) U.S. Cl. ........... 604/187; 528/73; 528/298; 528/307
(58) Field of Classification Search .................. 528/73, 528/298, 307; 604/187
See application file for complete search history.

(56) References Cited

U.S. PATENT DOCUMENTS

| 2001/0034419 A1 | 10/2001 | Kanayama et al. |
| 2003/0195303 A1 * | 10/2003 | Ikeda et al. .................. 525/418 |
| 2005/0209435 A1 | 9/2005 | Hirokane et al. |

FOREIGN PATENT DOCUMENTS

| EP | 1 445 019 A1 | 8/2004 |
| EP | 1 535 945 A1 | 6/2005 |
| JP | 2001 279085 | 10/2001 |
| JP | 2003 191929 | 7/2003 |
| JP | 2003 192797 | 7/2003 |
| JP | 2004 298220 | 10/2004 |
| JP | 2006 008805 | 1/2006 |
| WO | WO 01/21308 A1 | 3/2001 |
| WO | WO 01/21684 A1 | 3/2001 |

* cited by examiner

*Primary Examiner* — Ling Choi
*Assistant Examiner* — Gennadiy Mesh
(74) *Attorney, Agent, or Firm* — Oblon, Spivak, McClelland, Maier & Neustadt, L.L.P.

(57) ABSTRACT

Provided is a prefilled syringe comprising, as a resin constituting at least a barrel and a joint, a polyester resin that contains a diol unit having a cyclic acetal skeleton in an amount of from 1 to 30% by mol based on diol units and a dicarboxylic acid unit having a naphthalene skeleton in an amount of 70% by mol or more based on dicarboxylic acid units, and satisfies the following parameters: (i) a glass transition temperature of 110° C. or more measured with a differential scanning calorimeter, (ii) a moisture permeation coefficient of 1 g·mm/m$^2$/day or less, and (iii) an oxygen permeation coefficient of 10 cc·mm/m$^2$/day/atm or less.

18 Claims, No Drawings

PREFILLED SYRINGE

TECHNICAL FIELD

The present invention relates to an injection syringe having a drug solution filled hermetically in advance (i.e. prefilled syringe).

BACKGROUND ART

Glass has been used as a material for an injection syringe. However, glass may be broken by dropping, and is being progressively replaced by plastics, such as polycarbonate, polyethylene, polypropylene, cyclic olefin polymer and the like.

Upon using an injection syringe, such a method has been practiced that a drug solution is suctioned into a vacant injection syringe upon using. However, the method has problems of poor operation efficiency and occurrence of human errors, such as malpractice on filling a drug solution and the like, and is progressively replaced by a prefilled syringe having a prescribed amount of a drug solution filled in advance.

Although a material for a prefilled syringe is preferably plastics because of the aforementioned factors, there is restriction in use due to water vapor permeability (moisture permeability), oxygen permeability and adsorbability, which are inherent to plastics, and thus it is the current situation that replacement to plastics does not proceed.

For example, an injection syringe made from polycarbonate has a problem in that water content of a drug vaporizes due to moisture permeability thereof, and an injection syringe made of polypropylene or cyclic olefin polymer has a problem in that a drug solution is oxidized due to oxygen permeability thereof, or a particular component of the drug is diluted due to adsorbability thereof.

It is known that a polyester resin is small in oxygen permeability and adsorbability. Polyethylene naphthalate also has low moisture permeability, but cannot use as a syringe since it suffers dimensional change through partial crystallization upon boiling sterilization due to crystallinity thereof. There is no known polyester resin that has both heat resistance withstanding boiling sterilization and low moisture permeability.

Patent Document 1 discloses a prefilled syringe made of a synthetic resin having low adsorbability with a gasket using butyl rubber, but it is not sufficient in high heat resistance, low adsorbability, low moisture permeability and low oxygen permeability.

[Patent Document 1] JP-A-2004-298220

DISCLOSURE OF THE INVENTION

Problems to be Solved by the Invention

In view of the aforementioned problems, an object of the present invention is to provide a prefilled syringe that has high heat resistance, low moisture permeability, low oxygen permeability and low adsorbability.

Means for Solving the Problems

The present invention relates to a prefilled syringe containing, as a resin constituting at least a barrel and a joint, a polyester resin that contains a diol unit having a cyclic acetal skeleton in an amount of from 1 to 30% by mol based on diol units and a dicarboxylic acid unit having a naphthalene skeleton in an amount of 70% by mol or more based on dicarboxylic acid units, and satisfies the following (i) to (iii):

(i) a glass transition temperature of 110° C. or more measured with a differential scanning calorimeter, (ii) a moisture permeation coefficient of 1 g·mm/m²/day or less, and (iii) an oxygen permeation coefficient of 10 cc·mm/m²/day/atm or less.

Advantage of the Invention

The prefilled syringe of the present invention has high heat resistance, low moisture permeability, low oxygen permeability and low adsorbability, and is significantly improved in long-term storage stability as compared to a conventional plastic prefilled syringe.

BEST MODE FOR CARRYING OUT THE INVENTION

The present invention will be described in detail below.

At least a barrel and a joint of the prefilled syringe of the present invention is constituted by a resin including a polyester resin that contains a diol unit having a cyclic acetal skeleton in an amount of from 1 to 30% by mol based on diol units and a dicarboxylic acid unit having a naphthalene skeleton in an amount of 70% by mol or more based on dicarboxylic acid units.

Polyester Resin

The ratio of the diol unit having a cyclic acetal skeleton in the polyester resin used in the present invention is from 1 to 30% by mol. The diol unit having a cyclic acetal skeleton is contained in an amount of 1% by mol or more, whereby the glass transition temperature of the polyester resin is increased, and the polyester resin is improved in heat resistance. Furthermore, the crystallinity thereof is decreased, thereby preventing crystallization upon boiling sterilization, and dimensional change, whitening and embrittlement associated thereto from occurring. The ratio of the diol unit having a cyclic acetal skeleton is preferably 3% by mol or more, and more preferably 5% by mol or more. In the case where the ratio of the diol unit having a cyclic acetal skeleton in the polyester resin exceeds 30% by mol, it may not be preferred since the moisture permeability and the oxygen permeability of the polyester resin are increased. The ratio of the diol unit having a cyclic acetal skeleton is preferably 25% by mol or less, more preferably 22% by mol or less, further preferably 20% by mol or less, and still further preferably 15% by mol or less. Accordingly, the ratio of the diol unit having a cyclic acetal skeleton is preferably from 1 to 25% by mol, more preferably from 3 to 25% by mol, and further preferably from 5 to 22% by mol, from the standpoint of heat resistance and moisture permeability of the polyester resin.

The diol unit having a cyclic acetal skeleton in the diol units of the polyester resin used in the present invention is preferably a unit derived from a compound represented by the general formula (1) or the general formula (2):

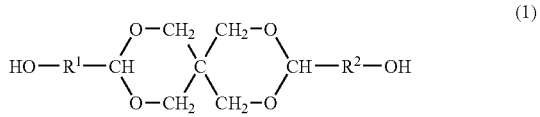

(1)

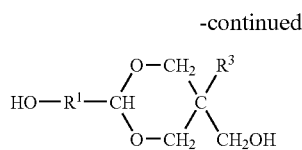

(2)

In the general formulae (1) and (2), $R^1$ and $R^2$ each independently represent a hydrocarbon group selected from the group consisting of an aliphatic hydrocarbon group having from 1 to 10 carbon atoms, an alicyclic hydrocarbon group having from 3 to 10 carbon atoms and an aromatic hydrocarbon group having from 6 to 10 carbon atoms. $R^1$ and $R^2$ each preferably represent a methylene group, an ethylene group, a propylene group, a butylene group or structural isomers of these groups. Examples of the structural isomers include an isopropylene group and an isobutylene group. $R^3$ represents a hydrocarbon group selected from the group consisting of an aliphatic hydrocarbon group having from 1 to 10 carbon atoms, an alicyclic hydrocarbon group having from 3 to 10 carbon atoms and an aromatic hydrocarbon group having from 6 to 10 carbon atoms. $R^3$ preferably represents a methyl group, an ethyl group, a propyl group, a butyl group or structural isomers of these groups. Examples of the structural isomers include an isopropyl group and an isobutyl group. Particularly preferred examples of the compound represented by the general formulae (1) and (2) include 3,9-bis(1,1-dimethyl-2-hydroxyethyl)-2,4,8,10-tetraoxaspiro[5.5]undecane, 5-methylol-5-ethyl-2-(1,1-dimethyl-2-hydroxyethyl)-1,3-dioxane and the like. The diol unit having a cyclic acetal skeleton may be constituted by one kind or two or more kinds thereof.

A diol constitutional unit other than the diol unit having a cyclic acetal skeleton is not particularly limited, and examples thereof include diol units derived from an aliphatic diol compound, such as ethylene glycol, trimethylene glycol, 1,4-butanediol, 1,5-pentanediol, 1,6-hexanediol, diethylene glycol, propylene glycol, neopentyl glycol and the like; an alicyclic diol compound, such as 1,3-cyclohexanedimethanol, 1,4-cyclohexanedimethanol, 1,2-decahydronaphthalenedimethanol, 1,3-decahydronaphthalenedimethanol, 1,4-decahydronaphthalenedimethanol, 1,5-decahydronaphthalenedimethanol, 1,6-decahydronaphthalenedimethanol, 2,7-decahydronaphthalenedimethanol, tetralindimethanol, norbornanedimethanol, tricyclodecanedimethanol, pentacyclododecanedimethanol and the like; a polyether compound, such as polyethylene glycol, polypropylene glycol, polybutylene glycol and the like; a bisphenol compound, such as 4,4'-(1-methylethylidene)bisphenol, methylenebisphenol (bisphenol F), 4,4'-cyclohexylidenebisphenol (bisphenol Z), 4,4'-sulfonylbisphenol (bisphenol S) and the like; an alkylene oxide adduct of the bisphenol compound; an aromatic dihydroxyl compound, such as hydroquinone, resorcin, 4,4'-dihydroxybiphenyl, 4,4'-dihydroxydiphenyl ether, 4,4'-dihydroxydiphenylbenzophenone and the like; an alkylene oxide adduct of the aromatic dihydroxyl compound; and the like. Diol units derived from ethylene glycol, trimethylene glycol, 1,4-butanediol, 1,4-cyclohexanedimethanol and the like are preferred, and an ethylene glycol unit is particularly preferred, from the standpoint of the mechanical strength and the heat resistance of the polyester resin, and availability of the diol. The diol constitutional unit other than the diol unit having a cyclic acetal skeleton may be constituted by one kind or two or more kinds thereof.

The ratio of the dicarboxylic acid unit having a naphthalene skeleton in the polyester resin used in the present invention is 70% by mol or more. The dicarboxylic acid unit having a naphthalene skeleton is contained in an amount of 70% by mol or more, whereby the glass transition temperature of the polyester resin is increased, i.e., the heat resistance thereof is enhanced, and simultaneously, the moisture permeation coefficient and the oxygen permeation coefficient are decreased. In the case where the ratio of the dicarboxylic acid unit having a naphthalene skeleton in the polyester resin is less than 70% by mol, it may not be preferred since the moisture permeation coefficient and the oxygen permeation coefficient of the polyester resin are increased and the heat resistance of the polyester resin is lowered. Accordingly, the ratio of the dicarboxylic acid unit having a naphthalene skeleton is preferably 85% by mol or more, and more preferably 95% by mol or more, from the standpoint of heat resistance, moisture permeability and oxygen permeability of the polyester resin.

Examples of the dicarboxylic acid unit having a naphthalene skeleton in the polyester resin used in the present invention include units derived from 1,3-naphthalenedicarboxylic acid, 1,4-naphthalenedicarboxylic acid, 1,5-naphthalenedicarboxylic acid, 2,6-naphthalenedicarboxylic acid, 2,7-naphthalenedicarboxylic acid and the like. The dicarboxylic acid unit having a naphthalene skeleton in the polyester resin may be constituted by one kind or two or more kinds thereof. A unit derived from 2,6-naphthalenedicarboxylic acid is most preferred among these from the standpoint of heat resistance and low moisture permeability.

A dicarboxylic acid unit other than the dicarboxylic acid unit having a naphthalene skeleton of the polyester resin used in the present invention is not particularly limited, and examples thereof include a unit derived from an aliphatic dicarboxylic acid, such as succinic acid, glutaric acid, adipic acid, pimelic acid, suberic acid, azelaic acid, sebacic acid, decanedicarboxylic acid, dodecanedicarboxylic acid, cyclohexanedicarboxylic acid, decalindicarboxylic acid, norbornanedicarboxylic acid, tricyclodecanedicarboxylic acid, pentacyclododecanedicarboxylic acid, 3,9-bis(1,1-dimethyl-2-carboxyethyl)-2,4,8,10-tetraoxaspiro[5.5]undecane, 5-carboxy-5-ethyl-2-(1,1-dimethyl-2-carboxyethyl)-1,3-dioxane, dimer acid and the like; and a unit derived from an aromatic dicarboxylic acid, such as terephthalic acid, isophthalic acid, phthalic acid, 2-methylterephthalic acid, biphenyldicarboxylic acid, tetralindicarboxylic acid and the like. A unit derived from an aromatic dicarboxylic acid is preferred from the standpoint of mechanical strength and heat resistance of the polyester resin, and a unit derived from terephthalic acid or isophthalic acid is particularly preferred from the standpoint of availability of the dicarboxylic acid. The dicarboxylic acid unit other than the dicarboxylic acid unit having a naphthalene skeleton of the polyester resin may be constituted by one kind or two or more kinds thereof.

The polyester resin may contain a unit derived from a monohydric alcohol, such as butyl alcohol, hexyl alcohol, octyl alcohol and the like, a unit derived from a polyhydric alcohol including a trihydric or higher alcohol, such as trimethylolpropane, glycerin, 1,3,5-pentanetriol, pentaerythritol and the like, a unit derived from monocarboxylic acid, such as benzoic acid, propionic acid, butyric acid and the like, a unit derived from polybasic carboxylic acid, such as trimellitic acid, pyromellitic acid and the like, and a unit derived from an oxy acid, such as glycolic acid, lactic acid, hydroxybutyric acid, 2-hydroxyisobutyric acid, hydroxybenzoic acid and the like, for controlling the melt viscoelasticity and the molecular weight, in such a range that does not impair the objects of the present invention.

In the polyester resin used in the present invention, it is preferred that the diol unit having a cyclic acetal skeleton is a unit derived from 3,9-bis(1,1-dimethyl-2-hydroxyethyl)-2,4,8,10-tetraoxaspiro[5.5]undecane, the diol constitutional unit other than the diol unit having a cyclic acetal skeleton is a unit derived from ethylene glycol, and the dicarboxylic acid constitutional unit is entirely a unit derived from 2,6-naphthalenedicarboxylic acid, particularly in consideration of high heat resistance, low moisture permeability, low oxygen permeability, mechanical strength and the like.

The polyester resin used in the present invention satisfies all the following (i) to (iii):

(i) a glass transition temperature of 110° C. or more measured with a differential scanning calorimeter, (ii) a moisture permeation coefficient of 1 g·mm/m$^2$/day or less, and (iii) an oxygen permeation coefficient of 10 cc·mm/m$^2$/day/atm or less.

As shown above, the glass transition temperature of the polyester resin used in the present invention is 110° C. or more, preferably 115° C. or more, and more preferably 120° C. or more, measured with a differential scanning calorimeter. In the case where the glass transition temperature of the polyester resin is in the range, the prefilled syringe of the present invention can be sterilized by boiling. The glass transition temperature of the polyester resin can be within the range by appropriately selecting the diol having a cyclic acetal skeleton and the dicarboxylic acid having a naphthalene skeleton, as described above. The upper limit of the glass transition temperature is not particularly determined and is generally 160° C. in consideration of the kinds of the constitutional units of the polyester resin and the composition thereof.

The moisture permeation coefficient of the polyester resin used in the present invention is 1 g·mm/m$^2$/day or less, preferably 0.9 g·mm/m$^2$/day or less, and more preferably 0.8 g·mm/m$^2$/day or less under a condition of 40° C. and 90% RH. In the case where the moisture permeation coefficient of the polyester resin is in the range, the prefilled syringe of the present invention can store a drug solution for a prolonged period of time. The moisture permeation coefficient of the polyester resin can be within the range by appropriately selecting the diol having a cyclic acetal skeleton and the dicarboxylic acid having a naphthalene skeleton, as described above.

The oxygen permeation coefficient of the polyester resin used in the present invention is 10 cc·mm/m$^2$/day/atm or less, preferably 7 cc·mm/m$^2$/day/atm or less, and more preferably 5 cc·mm/m$^2$/day/atm or less, under a condition of 23° C. and 65% RH. The oxygen permeation coefficient of the polyester resin is in the range, whereby a drug solution is prevented from suffering oxidation deterioration, thereby enhancing the storage stability. The oxygen permeation coefficient of the polyester resin can be within the range by appropriately selecting the diol having a cyclic acetal skeleton and the dicarboxylic acid having a naphthalene skeleton, as described above.

The polyester resin used in the present invention has low adsorbability as similar to other polyester resins, and substantially does not adsorb vitamin D and limonene.

The intrinsic viscosity (IV) of the polyester resin used in the present invention may be appropriately selected depending on the molding method and the purpose, and is preferably from 0.5 to 1.5 dL/g, more preferably from 0.5 to 1.2 dL/g, and further preferably from 0.5 to 1.0 dL/g, in terms of a value measured by using a mixed solvent of phenol and 1,1,2,2-tetrachloroethane at a mass ratio of 6/4 at 25° C. In the case where the intrinsic viscosity is in the range, the polyester resin used in the present invention is excellent in balance between the moldability and the mechanical performance.

The method for producing the polyester resin used in the present invention is not particularly limited, and any known production method of polyester may be applied. Examples of the method include a melt polymerization method, such as an ester exchange method, a direct esterification method and the like, a solution polymerization method, and the like. In the direct esterification method, there are some cases where it is necessary that a dicarboxylic acid is esterified with a diol having no cyclic acetal skeleton, and then after decreasing in acid value, it is reacted with the diol having a cyclic acetal skeleton. Among the production methods of the polyester resin described above, the ester exchange method is preferred from the standpoint of availability of raw materials.

Various catalysts, such as an ester exchange catalyst, an esterification catalyst, a polycondensation catalyst and the like, various stabilizers, such as an etherification preventing agent, a heat stabilizer, a light stabilizer and the like, a polymerization controlling agent and the like used upon producing the polyester resin may be those known in the art, and are appropriately selected depending on the reaction rate and the color, safety, heat stability, weather resistance, elution property and the like of the polyester resin. For example, examples of the catalysts include a compound (for example, an aliphatic acid salt, a carbonate salt, a phosphate salt, a hydroxide, a chloride, an oxide and an alkoxide) of a metal, such as zinc, lead, cerium, cadmium, manganese, cobalt, lithium, sodium, potassium, calcium, nickel, magnesium, vanadium, aluminum, titanium, antimony, tin and the like, metallic magnesium, and the like, which may be used solely or in combination of plural kinds thereof. The ester exchange catalyst for the ester exchange method is preferably a compound of manganese among those described above since it has high activity and suffers less side reaction, and the polycondensation catalyst is preferably a compound of antimony or titanium among those described above.

The polyester resin used in the present invention may contain various additives and molding assistants, such as an antioxidant, a light stabilizer, an ultraviolet ray absorbent, a plasticizer, an extender, a matting agent, a drying controlling agent, an antistatic agent, a sedimentation preventing agent, a surfactant, a flow improving agent, a drying oil, wax, a filler, a colorant, a reinforcing agent, a surface smoothing agent, a leveling agent, a curing reaction accelerator, a thickening agent and the like.

The prefilled syringe of the present invention will be described.

The prefilled syringe of the present invention can be produced by an injection molding method. The prefilled syringe of the present invention has no difference from an ordinary injection syringe, and is constituted by at least a barrel for filling a drug solution, a joint for joining an injection needle to one end of the barrel, and a plunger for extruding the drug solution at the time of using, in which it is necessary that at least the barrel and the joint are molded with a resin containing the polyester resin used in the present invention.

The resin containing the polyester resin preferably contains the polyester resin in an amount of 60% by mass or more, more preferably 80% by mass or more, and particularly preferably 100% by mass, from the standpoint of the advantages of the present invention. As a resin other than the polyester resin, for example, polypropylene, polyethylene, polycarbonate, cycloolefin polymer and the like may be contained.

In the prefilled syringe of the present invention, the barrel and the joint may be molded integrally, or members having been molded separately may be joined to each other. It is necessary to seal the tip of the joint, and the sealing method may be in such a manner or the like that the resin at the tip of the joint is heated to a molten state and pinched with a nipper or the like for fusion.

In the prefilled syringe of the present invention, a gasket may be used for enhancing the tightness between the plunger and the barrel. While the gasket may be formed with the polyester resin used in the present invention, a rubber elastic material is rather preferred, and examples thereof include butyl rubber, isoprene rubber, a thermoplastic elastomer and the like. In the case where the plunger is not in contact with the content owing to the use of the gasket or the like, examples of the resin that can be used for the plunger include, in addition to the polyester resin of the present invention, polypropylene, polyethylene, polycarbonate, cycloolefin polymer and the like. In the case where the plunger is in contact with the content, the polyester resin used in the present invention is preferably used for the plunger.

The prefilled syringe of the present invention has sufficient impact resistance that is equivalent or superior to a glass injection syringe.

The filling of the prefilled syringe of the present invention is not particularly limited and is preferably, for example, a lipophilic compound from the standpoint of the advantages of the present invention, and preferred examples thereof include a terpene compound, a protein and the like from the standpoint of usefulness of the compound. Specific examples of the terpene compound include a lipophilic vitamin, such as vitamin A, vitamin D, vitamin E, vitamin K and the like, a monoterpene, such as limonene, menthol, myrcene, ocimene, cosmene and the like, a sesquiterpene, such as farnesol, nerolidol, β-sinensal, caryophyllene and the like, a diterpene, sesterterpene, a triterpene, a tetraterpene and the like. Examples of the protein include albumin, such as egg albumin, serum albumin, milk albumin and the like. A terpene compound modified with a compound having peptide bond is also preferred as the filling, and examples thereof include paclitaxel and the like. The prefilled syringe of the present invention exhibits a small adsorption amount of these compounds upon filling these compounds.

EXAMPLE

The present invention will be described more specifically with reference to examples below, but the present invention is not limited in scope by the examples.

The evaluation methods for the polyester resins and the prefilled syringes used in the examples are as follows.

Evaluation Method of Polyester Resin (1) Ratio of Diol Unit Having Cyclic Acetal Skeleton and Dicarboxylic Acid Unit Having Naphthalene Skeleton The ratio of the diol unit having a cyclic acetal skeleton and the dicarboxylic acid unit having a naphthalene skeleton in the polyester resin was calculated from $^1$H-NMR measurement. The measurement was performed with JNM-AL400, produced by JEOL Ltd., at 400 MHz. The solvent used was deuterated chloroform.

(2) Glass Transition Temperature (Tg)

The glass transition temperature of the polyester resin was measured with DSC/TA-50WS, produced by Shimadzu Corporation, in such a manner that about 10 mg of the polyester resin was placed in an aluminum non-sealed container, heated to 280° C. at a temperature increasing rate of 20° C. per minute in a nitrogen gas (30 mL/min) stream for melting, and then rapidly cooled to provide a measurement specimen. The specimen was measured under the same conditions, and the temperature where the DSC curve changed by ½ of the difference between the base lines before and after the transition was designated as the glass transition temperature.

(3) Intrinsic Viscosity (IV)

A sample for measuring intrinsic viscosity was prepared in such a manner that 0.5 g of the polyester resin was dissolved by heating in 120 g of a mixed solvent of phenol and 1,1,2,2-tetrachloroethane (mass ratio: 6/4), and after filtering, it was cooled to 25° C. The measurement was performed with a capillary viscometer automatic measuring apparatus, SS-300-L1, produced by Shibayama Scientific Co., Ltd., at a temperature of 25° C.

(4) Moisture Permeation Coefficient

A film having a thickness of 200 μm obtained by melt-extrusion molding as a measurement specimen was measured for moisture permeability of the polyester resin. The measurement condition was 40° C. and 90% RH. The measurement apparatus was a water vapor permeability meter, L80-4005L, produced by Lyssy AG. The moisture permeation coefficient was calculated from the resulting moisture permeability according to the following expression.

$$\text{moisture permeation coefficient (g·mm/m}^2\text{/day)} = \text{moisture permeability (g/m}^2\text{/day)} \times \text{thickness (mm)}$$

(5) Oxygen Permeation Coefficient

A film having a thickness of 200 μm obtained by melt-extrusion molding as a measurement specimen was measured for oxygen permeability of the polyester resin. The measurement condition was 23° C. and 65% RH. The measurement apparatus was OX-TRAN 2/21, produced by Mocon, Inc. The oxygen permeation coefficient was calculated from the resulting oxygen permeability according to the following expression.

$$\text{oxygen permeation coefficient (cc·mm/m}^2\text{/day/atm)} = \text{oxygen permeability (cc/m}^2\text{/day/atm)} \times \text{thickness (mm)}$$

Evaluation Method of Prefilled Syringe (6) Transpiration Rate of Water

A prefilled syringe having water filled and sealed was stored in a constant temperature and humidity chamber at 40° C. and 75% RH for 3 months. The transpiration rate was measured from the mass of the syringe including the content W1 (before storing) and W2 (after storing) and the initial filled amount of water (w1) according to the following expression.

$$\text{transpiration rate of water (\%)} = ((W1-W2)/w1) \times 100$$

(7) Mass Increase of Nitrogen on Protein Adsorption Test

A prefilled syringe having a protein aqueous solution filled therein was stored at 23° C. and 50% RH for 8 days. The prefilled syringe after storing was washed five times with pure water and quantitatively determined for nitrogen amount (N2) by nitrogen elemental analysis. The difference between N2 and the nitrogen element amount (N1) before filling the protein aqueous solution was designated as the mass increase of nitrogen on protein adsorption test. The protein aqueous solution used was a 1% by weight aqueous solution of fraction V of albumin (bovine derived, powder), produced by Sigma-Ardrich Japan Co., Ltd. The elemental analysis was performed with a total nitrogen analyzer, TN-10, produced by Mitsubishi Chemical Corporation.

(8) Holding Ratio of Vitamin D

A prefilled syringe having a solution containing a prescribed amount (M1) of vitamin D filled was stored at 23° C.

and 50% RH for 8 days. The amount of vitamin D (M2) of the content after storing was quantitatively determined by liquid chromatography, and the holding ratio of vitamin D was calculated according to the following expression.

holding ratio of vitamin D (%)=(1−(M1−M2)/M1)× 100

(9) Drop Test

A prefilled syringe having water filled was freely dropped from a height of 1.5 m five times successively. A case where none of the samples among ten samples was broken was determined as being acceptable.

(10) Boiling Test

A prefilled syringe having water filled was sterilized by boiling in boiling water for 10 minutes, and then observed for leakage from between the plunger and the barrel and for appearance change, such as whitening and the like. A specimen that suffered none of them was determined as being acceptable.

Examples 1 to 3 and Comparative Examples 1 and 2

Production and Evaluation of Polyester Resin

The raw material monomers shown in Table 1 were charged in a 0.15 cubic meter polyester production apparatus equipped with a packed fractionating column, a partial condenser, a total condenser, a cold trap, an agitator, a heating device and a nitrogen introducing tube, and heated to 215° C. under a nitrogen atmosphere for performing ester exchange reaction in the presence of 0.03% by mol of manganese acetate tetrahydrate based on the dicarboxylic acid component. After making the reaction conversion of the dicarboxylic acid component to 90% or more, 0.02% by mol of antimony(III) oxide and 0.06% by mol of triethyl phosphate based on the dicarboxylic acid component were added, and temperature increase and depressurization were gradually conducted, thereby performing polycondensation finally at 280° C. and 0.1 kPa or less. The reaction was terminated when a suitable melt viscosity was obtained to produce a polyester resin.

The resulting polyester resin was molded by melt extrusion with a 25 mm single screw extruder equipped with a T-die at a temperature of from 240 to 260° C. to provide a film having a thickness of 200 μm.

The polyester resin and the film thus obtained were subjected to the aforementioned evaluations, and the results are shown in Table 1.

The abbreviations in the table have the following meanings.

NDCM: dimethyl 2,6-naphthalenedicarboxylate
DMT: dimethyl terephthalate
EG: ethylene glycol
SPG: 3,9-bis(1,1-dimethyl-2-hydroxyethyl)-2,4,8,10-tetraoxaspiro[5.5]undecane Production and Evaluation of Prefilled Syringe The polyester resin thus obtained was injection-molded with an injection molding machine with a clamping pressure of 100 t under a temperature conditions of from 240 to 260° C. to provide a barrel having a joint integrated therewith and a plunger. A gasket formed with butyl rubber was attached to the tip of the plunger to prepare an injection syringe having a capacity of 5 mL. The resulting injection syringe was subjected to the aforementioned evaluations, and the results are shown in Table 1.

Comparative Example 3

An injection syringe was prepared in the same manner as in Example 1 except that polypropylene, J-452HP, produced by Prime Polymer Co., Ltd., was used instead of the polyester resin, and subjected to the evaluations. The results of the evaluations are shown in Table 2.

Comparative Example 4

An injection syringe was prepared in the same manner as in Example 1 except that a cycloolefin copolymer, TOPAS 6013, produced by Ticona GmbH, was used instead of the polyester resin, and subjected to the evaluations. The results of the evaluations are shown in Table 2.

TABLE 1

|  |  | Example 1 | Example 2 | Example 3 | Comparative Example 1 | Comparative Example 2 |
|---|---|---|---|---|---|---|
| Charged amount of monomers (mol) | | | | | | |
| Dicarboxylic acid component | NDCM | 193.6 | 173.7 | 177.5 | — | 218.5 |
|  | DMT | — | — | 19.7 | 369.5 | — |
| Diol component | SPG | 19.4 | 34.7 | 19.7 | — | — |
|  | EG | 329 | 278 | 335.3 | 591.2 | 393.3 |
| Evaluation results of polyester resin | | | | | | |
| Copolymerization composition (% by mol) | NDCM | 100 | 100 | 90 | 0 | 100 |
|  | SPG | 10 | 20 | 10 | 0 | 0 |
| Glass transition temperature (Tg) (° C.) | | 127 | 130 | 128 | 84 | 124 |
| Intrinsic viscosity (IV) (dL/g) | | 0.65 | 0.66 | 0.67 | 0.75 | 0.65 |
| Moisture permeation coefficient (g · mm/m²/day) | | 0.72 | 0.76 | 0.9 | 8 | 0.44 |
| Oxygen permeation coefficient (cc · mm/m²/day/atm) | | 1.8 | 3.9 | 3.5 | 4 | 0.6 |
| Evaluation results of prefilled syringe | | | | | | |
| Transpiration rate of water (%) | | 0.6 | 0.7 | 0.8 | 7.5 | 0.4 |
| Mass increase of nitrogen (ppm) | | 6 | 6 | 6 | 5 | 5 |
| Vitamin D holding ratio (%) | | 100 | 100 | 100 | 100 | 100 |
| Drop test | | acceptable | acceptable | acceptable | acceptable | acceptable |
| Boiling test | | acceptable | acceptable | acceptable | whitening and deformation | whitening and leakage |

TABLE 2

|  | Comparative Example 3 | Comparative Example 4 |
| --- | --- | --- |
| Evaluation results of resin | | |
| Glass transition temperature (Tg) (° C.) | <−20 | 145 |
| Moisture permeation coefficient (g · mm/m²/day) | 0.28 | 0.06 |
| Oxygen permeation coefficient (cc · mm/m²/day/atm) | 75 | 40 |
| Evaluation results of prefilled syringe | | |
| Transpiration rate of water (%) | 0.2 | 0.1 |
| Mass increase of nitrogen (ppm) | 31 | 9 |
| Vitamin D holding ratio (%) | 89 | 89 |
| Drop test | acceptable | acceptable |
| Boiling test | acceptable | acceptable |

The invention claimed is:

1. A prefilled syringe comprising, as a resin constituting at least a barrel and a joint, a polyester resin that contains a diol unit having a cyclic acetal skeleton in an amount of from 1 to 30% by mol based on diol units and a dicarboxylic acid unit having a naphthalene skeleton in an amount of 70% by mol or more based on dicarboxylic acid units, and satisfies the following (i) to (iii):
  (i) a glass transition temperature of 110° C. or more measured with a differential scanning calorimeter,
  (ii) a moisture permeation coefficient of 1 g·mm/m²/day or less, and
  (iii) an oxygen permeation coefficient of 5 cc·mm/m²/day/atm or less.

2. The prefilled syringe according to claim 1, wherein the diol unit having a cyclic acetal skeleton is a diol unit derived from a diol represented by the general formula (1) or the general formula (2):

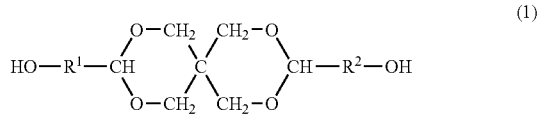

wherein R¹ and R² each independently represent a hydrocarbon group selected from the group consisting of an aliphatic hydrocarbon group having from 1 to 10 carbon atoms, an alicyclic hydrocarbon group having from 3 to 10 carbon atoms and an aromatic hydrocarbon group having from 6 to 10 carbon atoms,

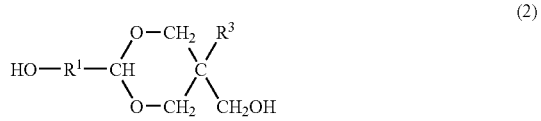

wherein R¹ is the same as the above and R³ represents a hydrocarbon group selected from the group consisting of an aliphatic hydrocarbon group having from 1 to 10 carbon atoms, an alicyclic hydrocarbon group having from 3 to 10 carbon atoms and an aromatic hydrocarbon group having from 6 to 10 carbon atoms.

3. The prefilled syringe according to claim 1, wherein the diol unit having a cyclic acetal skeleton is a diol unit derived from 3,9-bis(1,1-dimethyl-2-hydroxyethyl)2,4,8,10-tetraoxaspiro [5.5]undecane or 5-methylol-5-ethyl-2-(1,1-dimethyl-2-hydroxyethyl)1,3-dioxane.

4. The prefilled syringe according to claim 1, wherein the dicarboxylic acid unit is derived from at least one dicarboxylic acid selected from the group consisting of 1,3-naphthalenedicarboxylic acid, 1,4-naphthalenedicarboxylic acid, 1,5-naphthalenedicarboxylic acid, 2,6-naphthalenedicarboxylic acid and 2,7-naphthalenedicarboxylic acid.

5. The prefilled syringe according to claim 1, wherein the dicarboxylic acid unit is derived from 2,6-naphthalenedicarboxylic acid.

6. The prefilled syringe according to claim 1, wherein the polyester resin has an intrinsic viscosity (IV) in a range of from 0.5 to 1.5 dL/g at 25° C.

7. The prefilled syringe according to claim 1, wherein the polyester resin is produced by an ester exchange method.

8. The prefilled syringe according to claim 1, wherein the polyester resin that contains a diol unit having a cyclic acetal skeleton in an amount of from 1 to 25% by mol based on diol units.

9. The prefilled syringe according to claim 1, wherein the polyester resin that contains a diol unit having a cyclic acetal skeleton in an amount of from 3 to 25% by mol based on diol units.

10. The prefilled syringe according to claim 1, wherein the polyester resin that contains a diol unit having a cyclic acetal skeleton in an amount of from 5 to 22% by mol based on diol units.

11. The prefilled syringe according to claim 1, wherein the polyester resin contains a diol unit derived from at least one of an aliphatic diol compound, an alicyclic diol compound, a polyether compound, a bisphenol compoundan alkylene oxide adduct of a bisphenol compound and an aromatic dihydroxyl compound.

12. The prefilled syringe according to claim 1, wherein the polyester resin contains a diol unit derived from at least one of ethylene glycol, trimethylene glycol, 1,4-butanediol and 1,4-cyclohexanedimethanol.

13. The prefilled syringe according to claim 1, wherein the polyester resin contains a dicarboxylic acid unit having a naphthalene skeleton in an amount of 85% by mol or more based on dicarboxylic acid units.

14. The prefilled syringe according to claim 1, wherein the polyester resin contains a dicarboxylic acid unit having a naphthalene skeleton in an amount of 95% by mol or more based on dicarboxylic acid units.

15. The prefilled syringe according to claim 1, wherein the polyester resin contains a dicarboxylic acid unit derived from at least one of an aliphatic dicarboyxlic acid and an aromatic dicarboxylic acid.

16. The prefilled syringe according to claim 1, wherein the polyester resin has a glass transition temperature of 110° C. to 160° C.

17. The prefilled syringe according to claim 1, wherein the polyester resin has a a moisture permeation coefficient of 0.9 g·mm/m²/day or less.

18. The prefilled syringe according to claim 1, wherein the polyester resin has a a moisture permeation coefficient of 0.8 g·mm/m²/day or less.

* * * * *